(12) United States Patent  (10) Patent No.: US 8,435,451 B2
Al-Mahnna  (45) Date of Patent: May 7, 2013

(54) PORTABLE INCENSE BURNER AND STORAGE DEVICE

(76) Inventor: Khaled Abdullah Al-Mahnna, Salmiya (KW)

( * ) Notice: Subject to any disclaimer, the term of this patent is extended or adjusted under 35 U.S.C. 154(b) by 664 days.

(21) Appl. No.: 12/605,659

(22) Filed: Oct. 26, 2009

(65) Prior Publication Data

US 2011/0097242 A1 Apr. 28, 2011

(51) Int. Cl.
*A62B 7/08* (2006.01)
*A61L 2/04* (2006.01)
*A61L 9/02* (2006.01)
*A01N 25/00* (2006.01)
*A61K 9/72* (2006.01)

(52) U.S. Cl.
USPC ........... 422/126; 422/124; 422/125; 422/307; 424/40

(58) Field of Classification Search .................. 422/124, 422/125, 126, 307; 424/40
See application file for complete search history.

(56) References Cited

U.S. PATENT DOCUMENTS

| | | | | |
|---|---|---|---|---|
| 3,058,178 A | * | 10/1962 | Campagna | 422/126 |
| 4,237,097 A | * | 12/1980 | McDuffie | 422/126 |
| 6,354,710 B1 | * | 3/2002 | Nacouzi | 362/96 |
| 7,736,605 B1 | * | 6/2010 | Gomez | 422/306 |

* cited by examiner

*Primary Examiner* — Walter D Griffin
*Assistant Examiner* — Christopher Vandeusen
(74) *Attorney, Agent, or Firm* — Richard C. Litman

(57) ABSTRACT

An incense burner and storage device includes a lower housing with a base and a storage compartment. The device also includes an upper housing and an upwardly extending column for supporting the upper housing. The upper housing includes a support for charcoal and incense and an ashtray for collecting ashes. The ashtray is also rotatable about a vertical axis between a loading position and a burning position. The ashtray also includes a perforated screen-like bottom that allows a flame to pass therethrough. A cigarette lighter is used for heating the charcoal and is pivotally mounted within the column for removal and replacement of the lighter. An adjustment mechanism is fixed to one side of the upper portion of the column and allows the charcoal and incense support to be raised or lowered with respect to the cigarette lighter.

7 Claims, 1 Drawing Sheet

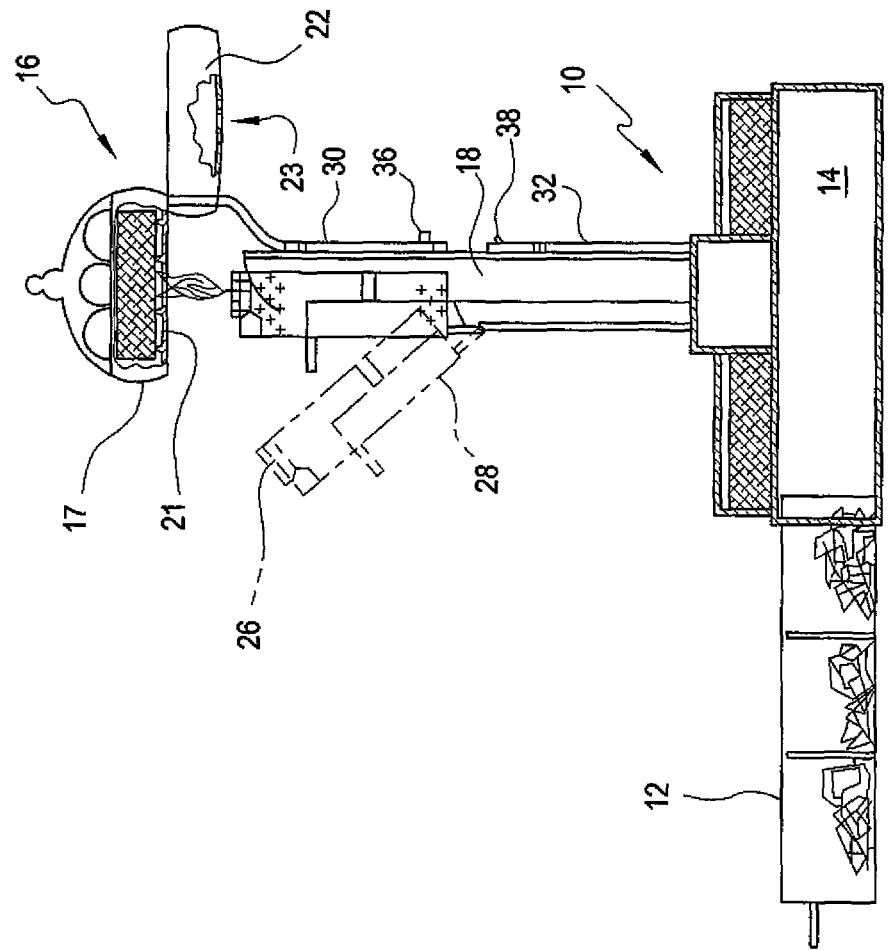
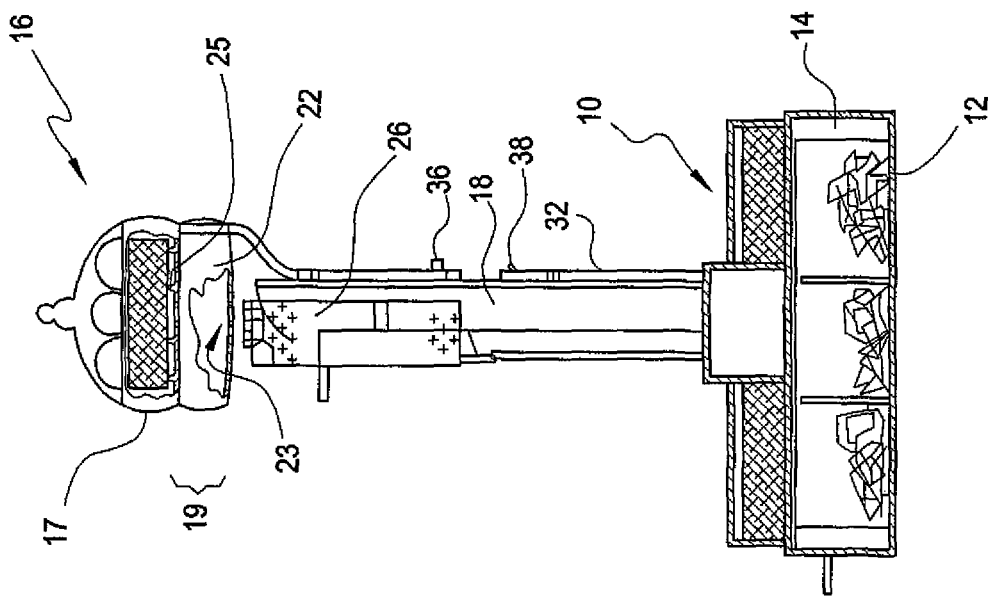

PORTABLE INCENSE BURNER AND STORAGE DEVICE

FIELD OF THE INVENTION

This invention relates to a portable incense burner and storage device and more particularly to a self-contained incense burner and storage device for safely holding, igniting and burning incense and at the same time storing incense and charcoal means for igniting the charcoal.

BACKGROUND FOR THE INVENTION

Incense burners are well known and have been in use for many years. Burners of various designs are appropriate for different applications ranging from religious services to a device for killing flying insects and/or dispensing a pleasant aroma.

For example, a U.S. Pat. No. 3,058,178 of Campagna relates to a portable incense burner that is particularly well suited for use in religious ceremonies. Early burners placed burning charcoals in a portable receptacle provided with holes in the wall to permit air to pass to the charcoal to keep it burning and to permit the escape of incensed fumes. Incense is placed over the burning coal to produce the fumes. In order to overcome a problem associated with receptacles becoming very hot on the outer surface, and the inconvenience of refilling at an inconvenient time, Campagna teaches the use of an electrical socket and a thermostat to control the heat applied to the incense.

A more recent patent Rogers, U.S. Pat. No. 4,198,375 discloses an incense burner consisting of an exterior receptacle fitted with an ash collecting basket and supporting a cigarette lighter within the receptacle together with an axially disposed spindle. A disc having a plurality of circumferentially disposed holes dimensioned to accept sticks of incense is supplied on the spindle above the receptacle and a wire meshed cap is fitted over the disc at the top of the receptacle. The disc can be rotated to permit selective ignition of one or more incense sticks.

An even more recent patent of Gaines, U.S. Pat. No. 6,495,107 discloses an incense burner comprising a base portion and a removable tapered stack portion and which includes an electric fan to dispose incense smoke. The base portion defines a fan retention cavity configured to retain the electric fan. Attached to the top of the electric fan is a vented platform containing a plurality of vents and an incense retainer aperture. An incense retainer retains an ignited dip stick of incense and is positioned into the incense retainer aperture. A tapered stack which includes a smoke retardant ring is removably positioned on top of the vented platform. The electric fan is switched on thereby causing the incense smoke to present itself in a pleasing manner.

Notwithstanding the above it is presently believed that there is a potential demand and a commercial market for an incense burner and storage device in accordance with the present invention. There should be a demand because such burners and storage devices combine a traditional burner in that the incense is disposed on a piece of burning charcoal with a storage device for incense, charcoal and flame supporting means. The burner and storage device also incorporate a pair of tweezers for adding incense and/or charcoal without the risk of burning oneself. In addition, the burner and storage device also provides an easily replaceable disposable cigarette lighter without departing from the appearance of the device. Finally the burner and storage device is durable, includes ceramic elements that are exposed to a flame and are long lasting construction.

BRIEF SUMMARY OF THE INVENTION

In essence an incense burner and storage device in accordance with the present invention includes a lower housing with a base and a storage compartment above the base for storing incense, charcoal and flame supporting means, as for example one or more disposable cigarette lighters. The incense burner and storage device also includes an upper housing and an upwardly extending column having an upper and a lower portion. The column is fixed to the base and extends upwardly therefrom for supporting the upper housing above and at a slight distance from the lower housing. The upper housing includes a ceramic support for charcoal and incense and an ashtray for collecting ashes remaining after the charcoal and incense have been burned. The ashtray is rotatable about a vertical axis between a loading position and a burning position with the ashtray disposed below the support with a screen like bottom that allows a flame to pass therethrough. An important feature of the present invention resides in a flame supporting means, namely a disposable cigarette lighter for heating and igniting the charcoal and a pivotal port for allowing the cigarette lighter to be rotated about a horizontal axis at a base thereof to insert or remove the lighter from the burner. An adjustment mechanism is also fixed to a side of the column and includes an adjustment mechanism for moving the charcoal up or down with respect to the flame. It also allows the pivotal mount to rotate outwardly from the column to an angle of about 45 degrees to allow the cigarette lighter to be inserted or removed from the column. In a preferred embodiment of the invention means such as a hook are provided on the lower portion of the column for holding the pair of tweezers.

The invention will now be described in connection with the following drawings wherein like numbers have been used to identify like parts.

DESCRIPTION OF THE DRAWINGS

FIG. 1 is a cross-sectional view of an incense burner and storage device in accordance with a preferred embodiment of the invention with a lighter and ashtray in a position wherein the charcoal and the incense are burned; and FIG. 2 is cross-sectional view of the device shown in FIG. 1, but with the ashtray and support for a cigarette lighter rotated outwardly for removal of ashes and replacement of the cigarette lighter.

DESCRIPTION OF THE PREFERRED EMBODIMENT OF THE INVENTION

As illustrated in FIGS. 1 and 2 a portable incense burner and storage device in accordance with a preferred embodiment of the invention includes a lower housing 10 having a metal base 12 and a metal storage compartment 14 for storing different types of incense, charcoal or the like and a plurality of relatively small disposable cigarette lighters, candles or the like. In the preferred embodiment of the invention the storage compartment 14 is a drawer that is divided into three compartments for two different types of incense and a plurality of small disposable cigarette lighters with an area above the drawer adapted to receive and hold a supply of charcoal.

An upper metal housing 16 and an upwardly extending column 18 with upper and lower portions 17 and 19 is fixed to the metal base 12 an extends upwardly from the upper base 12 to support the upper metal housing 16 above and at a distance from the lower housing 10. The upper housing 16 includes a ceramic support member 21 and a rotatable ceramic ashtray 22. The bottom 23 of the ashtray 22 has a grid like structure resembling an array of perforations, small openings that are dimensioned to let a flame pass through the openings and yet small enough to prevent ashes from falling through the gratings. This grid like structure may be checkered or define round holes that are relatively thin since the ashes have very little weight. The support member includes an open grid with a plurality of upwardly projecting teeth 25 for supporting a piece of charcoal thereon. Incense is then sprinkled on top of the charcoal.

The rotatable ashtray 22 rotates about a generally vertical axis in a general horizontal plane and may be readily removed from the column 18 by a conventional mechanism.

The rotatable ashtray rotates between a loading or unloading position and a burning position and may be modified to carry the grid for supporting the piece of charcoal.

A cigarette lighter 26 is disposed in an upper portion 17 of the column 18 and a pivotable support 28 that rotates about a horizontal axis allows the cigarette lighter 26 to be recessed into the column 18 in a burn position and rotated about the pivot by an angle of up to about 45 degrees for replacement of the cigarette lighter.

An important feature of the present invention resides in the upper metal housing 16 being adjustably support by the adjustment mechanisms 30, 36 that are fixed to a side of the upper portion of the column 18 for raising and lowering the upper metal housing 16 with respect to the flame.

A pair of tweezers 32 is also disposed on the side of the column 18 by means of hook 38 and may be readily removed for adding charcoal and/or incense to the burner without risk of burning an individual's hand.

While the invention has been described in connection with its accompanying drawings it should be recognized that changes and modifications may be therein without departing from scope of the appended claims.

What is claimed is:

1. A portable incense burner and storage device comprising:

a lower housing including a base and a storage compartment for storing at least incense and charcoal, the base having a bottom surface and the storage compartment comprising a drawer;

an upper housing and an upwardly extending column having an upper portion and a lower portion fixed to the base and extending upwardly therefrom for supporting the upper housing above and at a distance from the lower housing;

the upper housing including an incense and charcoal support and an ashtray, and a cover disposed over the incense and charcoal support and the ashtray and wherein the incense and charcoal support is rotatable about a vertical axis from an incense and charcoal loading position away from the cover to a burning position beneath and in line with the cover;

flame supporting means and a pivotal mechanism disposed in the upper portion of the column for positioning the flame supporting means under the charcoal and incense support and wherein the pivotal mechanism is rotated about a generally horizontal axis; and an adjustment mechanism fixed to a side of the upper portion of the column for raising and lowering the charcoal and incense support with respect to the flame supporting means.

2. A portable incense burner and storage device according to claim 1 in which the flame supporting means is a cigarette lighter.

3. A portable incense burner and storage device according to claim 1 which includes a metal storage area above the drawer for storing charcoal.

4. A portable incense burner and storage device according to claim 1 in which the cover and the upper housing are made from metal.

5. A portable incense burner and storage device according to claim 1 which includes a pair of tweezers removably attached to the lower portion of the column.

6. A portable incense burner and storage device according to claim 1 in which the cover is positioned over the charcoal and incense support and includes a number of openings therein.

7. A portable incense burner and storage device according to claim 1 in which the charcoal support includes a plurality of upwardly extending teeth for supporting charcoal and incense above the ashtray.

* * * * *